US007530151B2

(12) United States Patent
Osawa

(10) Patent No.: US 7,530,151 B2
(45) Date of Patent: May 12, 2009

(54) VIBRATOR ARRAY, MANUFACTURING METHOD THEREOF, AND ULTRASONIC PROBE

(75) Inventor: Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 134 days.

(21) Appl. No.: 11/353,138

(22) Filed: Feb. 14, 2006

(65) Prior Publication Data

US 2006/0181177 A1 Aug. 17, 2006

(30) Foreign Application Priority Data

Feb. 14, 2005 (JP) ............................ 2005-036438
Nov. 24, 2005 (JP) ............................ 2005-339025

(51) Int. Cl.
*H04R 17/00* (2006.01)
*A61B 8/12* (2006.01)

(52) U.S. Cl. ........................ 29/25.35; 367/165; 367/173

(58) Field of Classification Search ................. 310/322, 310/311, 334; 156/250, 325; 29/25.35; 600/459; 367/118, 140, 173, 176, 905, 162, 165, 153
See application file for complete search history.

(56) References Cited

U.S. PATENT DOCUMENTS 3,964,014 A * 6/1976 Tehon ........................ 367/155
4,122,725 A * 10/1978 Thompson ................... 73/632
4,254,661 A * 3/1981 Kossoff et al. ................ 73/625
5,042,493 A * 8/1991 Saito et al. .................. 600/459
5,101,133 A * 3/1992 Schafer ...................... 310/335
5,327,895 A * 7/1994 Hashimoto et al. .......... 600/459
5,428,382 A * 6/1995 Shimosato et al. ............ 347/71
6,483,225 B1 11/2002 Spigelmyer
6,558,332 B1 * 5/2003 Shimizu ..................... 600/459
2004/0104642 A1 * 6/2004 Takeuchi et al. ............ 310/328

FOREIGN PATENT DOCUMENTS

EP 0524749 A 1/1993
JP 2001-46368 A 2/2001

* cited by examiner

*Primary Examiner*—Thomas H Tarcza
*Assistant Examiner*—Lisa Yung
(74) *Attorney, Agent, or Firm*—Sughrue Mion, PLLC

(57) ABSTRACT

In an ultrasonic transducer array, a plurality of vibrators arranged in an array is bonded to a base plate by bond material. The bond material bonds the bottom of the each vibrator to the base plate in a manner to surround lower part of the side face of the vibrator. A filling material is filled in between the vibrators. The filling material has a multi-layer structure of different rigidity. In a double layer structure of the filling material, it is preferable that thickness ratio of layer of filling material at the base plate side (lower side) to the other layer of the filling material is 1:1 to 1:3. Preferably, a beam is provided for connecting the side faces of the adjacent vibrators.

8 Claims, 8 Drawing Sheets

VIBRATOR ARRAY, MANUFACTURING METHOD THEREOF, AND ULTRASONIC PROBE

FIELD OF THE INVENTION

The present invention relates to a vibrator array having a base plate on which a plurality of vibrators is arranged in an array manner, and relates to a manufacturing method thereof and an ultrasonic probe having the vibrator array.

BACKGROUND OF THE INVENTION

An ultrasonic transducer array built in an ultrasonic probe is known as a vibrator array having a plurality of vibrators arranged in an array manner on a base plate. The ultrasonic transducer array includes a backing material as a base plate, piezoelectric elements as vibrators, an electrode, and an acoustic impedance matching layer.

In manufacturing of the ultrasonic transducer array, a wafer of, for example, PZT (lead zirconium titanate) which is a material of the piezoelectric elements is bonded to the backing material by an adhesive. After the electrode, the acoustic impedance matching layer and the like are stacked on the wafer, grooves are made on the wafer by dicing process at predetermined intervals to reach a part of the backing material from the acoustic impedance matching layer. The wafer is divided into a plurality of piezoelectric elements with the grooves. Filling materials are filled in the grooves and the ultrasonic transducer array is completed.

In the ultrasonic transducer array, each piezoelectric element vibrates at high speed in the thickness direction to generate ultrasounds. When it vibrates in the thickness direction, vibrations in the width direction also occur. There is a problem that such width directional vibrations unstabilize the vibration action of each piezoelectric element in the thickness direction and thus negatively influence acoustic characteristics of the ultrasonic transducer array.

In order to solve the above problem, Japanese Patent Laid-Open Publication No. 2001-046368 discloses a manufacturing method of an ultrasonic probe which has piezoelectric elements formed in an almost trapezoid to gradually increase the width toward the backing material to restrain the unnecessary vibrations of the piezoelectric elements in width direction.

However, in the method disclosed in Japanese Patent Laid-Open Publication No. 2001-046368, the piezoelectric elements are thermally deformed by friction heat on the dicing process. In order to solve the problem, polishing powder such as alumina powder is mixed in the backing material, therefore cost increases.

SUMMARY OF THE INVENTION

A primary object of the present invention is to provide a vibrator array for restraining vibrations of the vibrators in the width direction without extra manufacturing cost, and to provide a manufacturing method thereof.

Another object of the present invention is to provide an ultrasonic probe which improves workability on manufacturing and enhances reliance of the product.

To achieve the above and other objects, in the vibrator array of the present invention, the bottom of each vibrator is bonded to the base plate in a manner that lower part of a side face of each vibrator is surrounded by a bond material.

The bond material has conductivity. Silver paste is preferably used as the bond material. The thickness of the bond material is preferably 10 to 20% of the thickness of each vibrator. A filling material is filled in between each vibrator. It is preferable that the filling material has multiple layer structure of different rigidity. In a double-layer structure of the filling material, the ratio of the thickness of the bottom (lower side) of each vibrator to the upper side thereof is preferably 1:1 to 1:3. A beam is preferably provided for connecting the side face of each vibrator. The beam is provided at the suitable position, for example, the central part of the side face, the upper part of the side face, and the upper face of each vibrator.

A manufacturing method of the present invention comprises steps of: subdicing a wafer to form a plurality of vibrators; applying a bond material to the base plate; and bonding the bottom of each vibrator to the wafer by the bond material in a manner that lower part of a side face of each vibrator is surrounded by the bond material. The upper portion of the wafer which connects the upper parts of the vibrators is removed to separate the vibrators. A filling material is filled in between the vibrators. The filling material has a multilayer structure of different rigidity.

An ultrasonic probe of the present invention has a vibrator array. The bottom of each vibrator array is bonded to the base plate in a manner that the lower part of the side face of each vibrator arranged in an array is surrounded by the bond material. The bond material has conductivity. Silver paste is preferable as the bond material. A filling material is filled in gaps each vibrator. The filling material has a multi-layer structure of different rigidity. The base plate is attached to the base in a form of concavity, convexity or cylinder.

According to the present invention, the lower part of the side face of each vibrator is surrounded by the bond material used for bonding the vibrators to the base plate, so that vibration of the vibrator in the width direction can be restrained.

Moreover, the vibrator array of the present invention is built in as an ultrasonic transducer array, therefore workability on manufacturing can be improved and the reliance of the product can be enhanced.

DESCRIPTION OF THE PREFERRED EMBODIMENTS

Figure 1A:
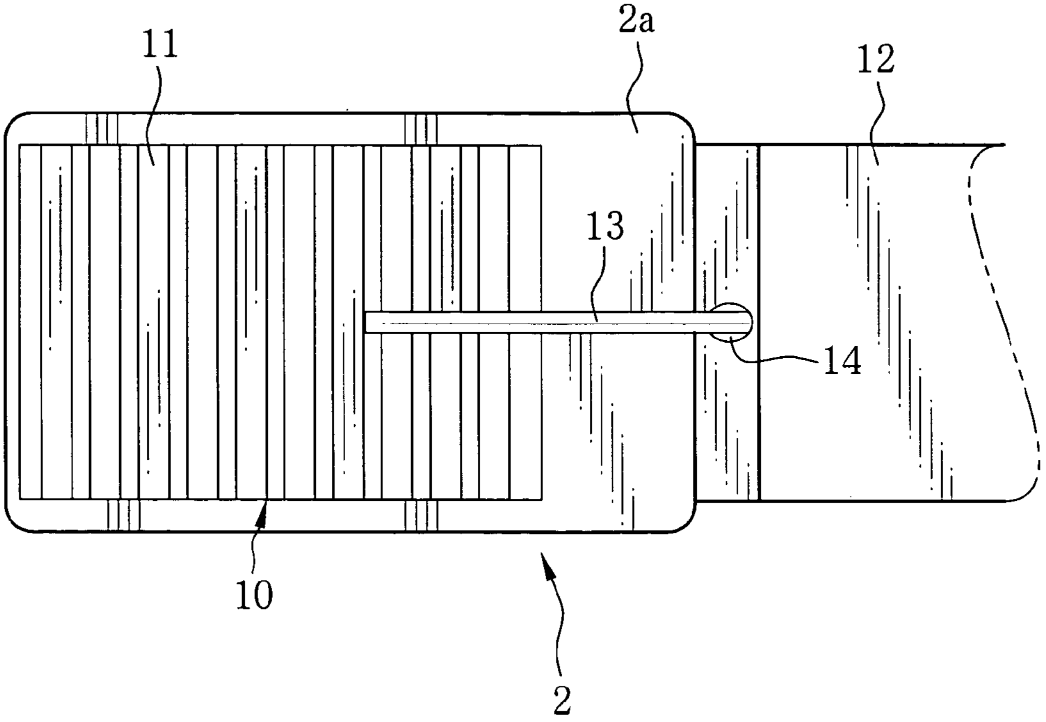
FIG. 1A is a plan view of a one-dimensional ultrasonic transducer array.
Figure 1B:
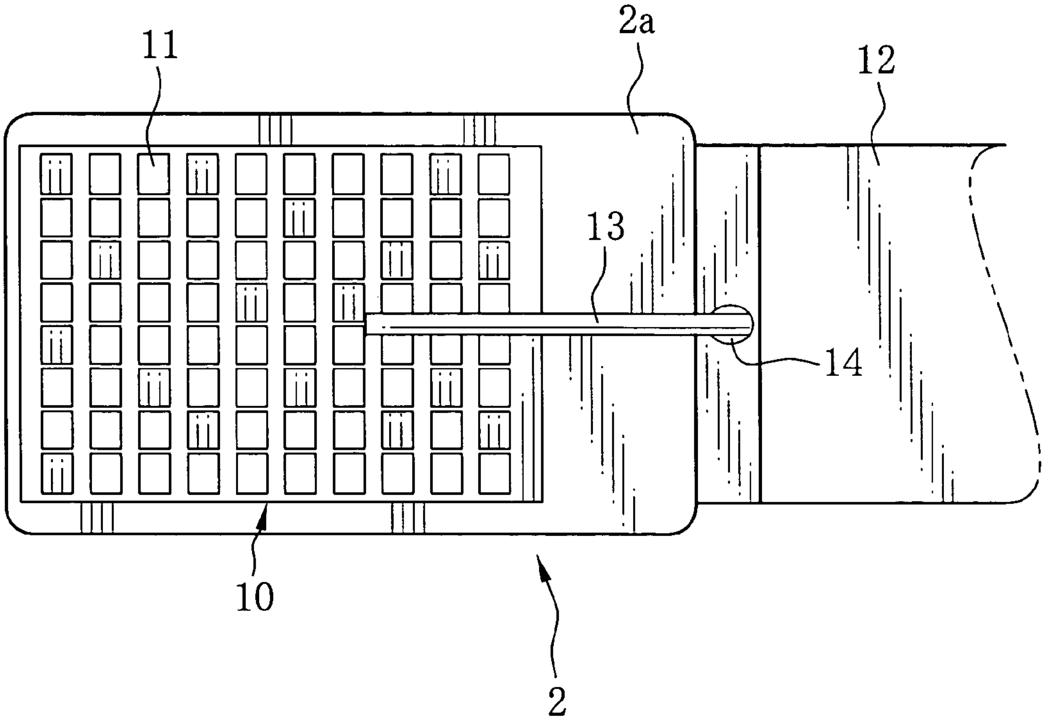
FIG. 1B is a plan view of a two-dimensional ultrasonic transducer array.

In FIGS. 1A and 1B, an ultrasonic transducer array 10 of convex electronic scanning type is disposed at a tip 2*a* of an ultrasonic probe 2. In the ultrasonic transducer array 10, a plurality of ultrasonic transducers 11 is arranged in either one-dimensional array state as shown in FIG. 1A or two-dimensional array state as shown in FIG. 1B. In the ultrasonic transducer array 10, a backing material 21 (see FIG. 2) is bonded to a curved surface of a supporting member 20 (see FIG. 2) which is cylindrically formed.

An imaging device for capturing optical image of an internal body part is mounted in a sheath 12 connected to the ultrasonic transducer array 10. The imaging device includes an optical system mounted to the sheath 12 and an image sensor disposed inside the sheath 12. The sheath 12 is provided with an exit end of a light guide for illuminating the internal body part. A channel for a wearing needle 14 is provided at the central part of the sheath 12. Array wiring cables for electrically connecting an ultrasound observing device to the ultrasonic transducer array 10, and ultrasonic transducer array 10 to an endoscope monitor, and an image device wiring cable for electrically connecting an endoscope monitor to the imaging device are inserted inside the sheath 12.

Figure 2:
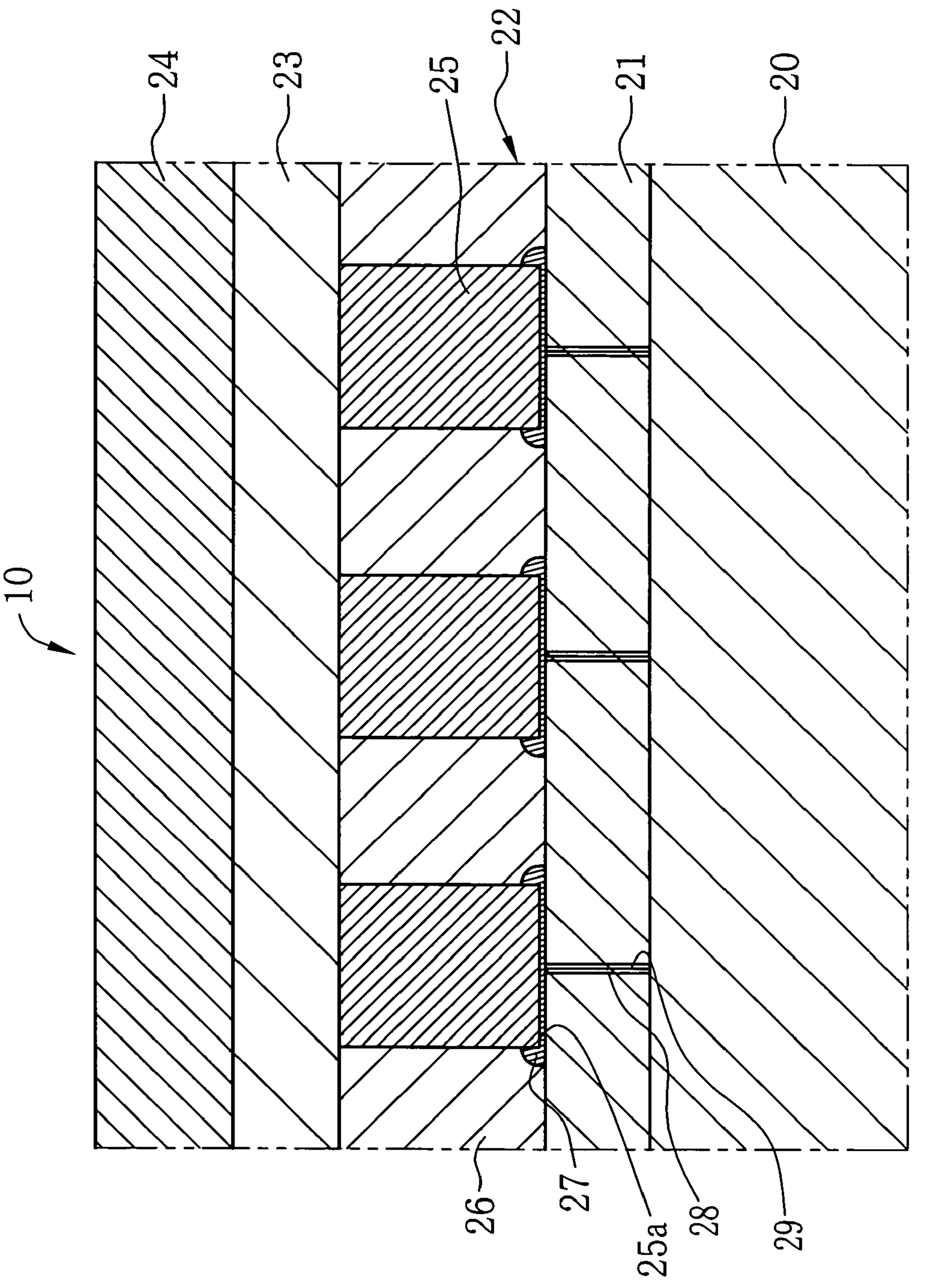
FIG. 2 is an enlarged sectional view of an ultrasonic transducer array.
Figure 3:
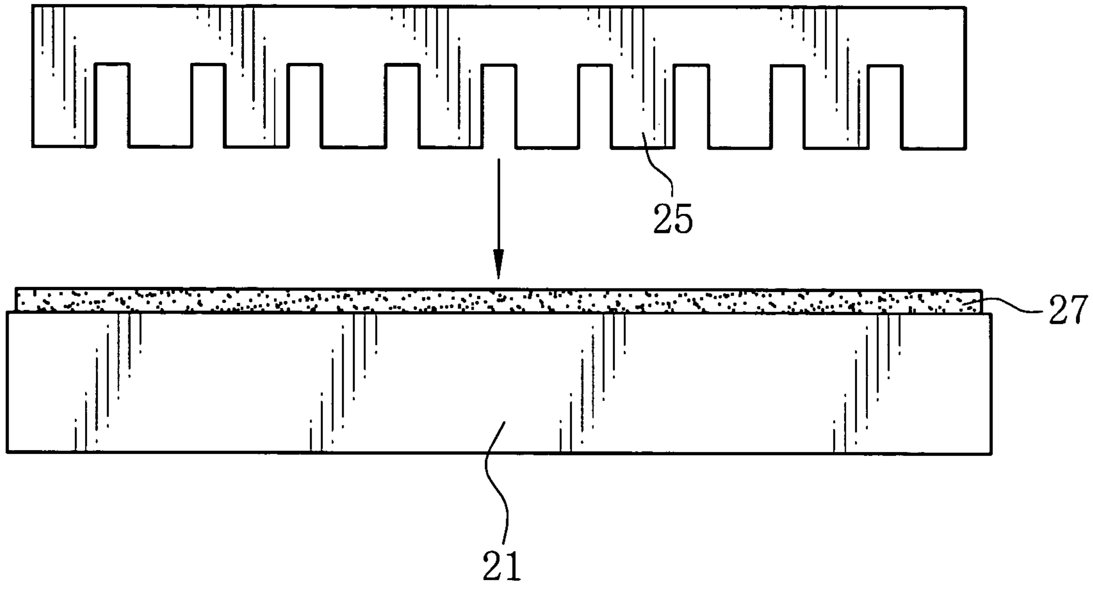
FIG. 3 is an explanatory view showing a process of laying a wafer of diced piezoelectric elements on a flat layer made of a silver paste formed on a backing material.

In FIG. 2, the ultrasonic transducer array 10 has a structure that the backing material 21, a piezoelectric element array 22, an acoustic impedance matching layer 23 and an acoustic lens 24 are overlaid on the supporting member 20 in sequence on one another.

The piezoelectric element array 22 consists of piezoelectric elements 25 arranged one-dimensionally or two-dimensionally and a filling material 26 filled in gaps between the adjacent piezoelectric elements 25. Each piezoelectric element 25 has a thickness of, for example, 300 to 500 μm and a width of, for example, 300 μm, and an interval between each piezoelectric element 25 is, for example 50 μm. For example, an epoxy resin, an urethane resin, or a silicon resin is used for the filling material 26. The silicon resin may be "silicone rubber" (product name, produced by Shin-Etsu Chemical Co., Ltd.).

The backing material 21 and the piezoelectric elements 25 are bonded by silver paste 27. A lower part of a side face 25*a* of each piezoelectric element 25 is surrounded by the silver paste 27. For example, product name, "NH-050A", "NH-060A", "NH-070A" (produced by NIHON HANDA CO., LTD.) or product name,"H20S" (produced by Epoxy Technology) are used for the silver paste 27. The silver paste 27 has conductivity of approximately $3.1\times10^{-4}$ [Ω·cm], and preferably $10\times10^{-2}$ to $10^{-4}$ [Ω·cm].

The backing material 21 consists of a flexible sheet of, for example, polyimide. The backing material 21 is provided with through holes 28, which penetrate to the piezoelectric element array 22 from the bottom of the backing material 21. Wires 29 (approximately 80 μm in a diameter) extending from the array wiring cable are inserted in the through holes 28, and connected to individual electrodes (not shown) of the piezoelectric elements 25 through the silver paste 27.

The acoustic impedance matching layer 23 is provided for reducing a difference in acoustic impedance between the piezoelectric elements 25 and the living body. The acoustic lens 24 is made of, for example, a silicon resin, and overlaid on a common electrode (exemplary embodiments of which are shown in FIGS. 8-11) of the piezoelectric elements 25, such that the ultrasounds generated from the ultrasonic transducer array 10 are focused to an internal body part. The acoustic lens 24 may not be used, or a protective layer may be provided in place of the acoustic lens 24.

In manufacturing of the ultrasonic transducer array 10, a film of the silver paste 27 having a uniform thickness (approximately 30 μm which is 10 to 20% of the thickness of the piezoelectric elements 25) is formed on the backing material 21 by using a squeegee, a doctor blade or a screen-printing process. A subdiced wafer of the piezoelectric elements 25 provided with the individual electrodes 30 is laid on the film, and the silver paste 27 is hardened. Thereby, the lower part of the side face 25*a* of each piezoelectric element 25 is surrounded by the silver paste 27.

Figure 4:
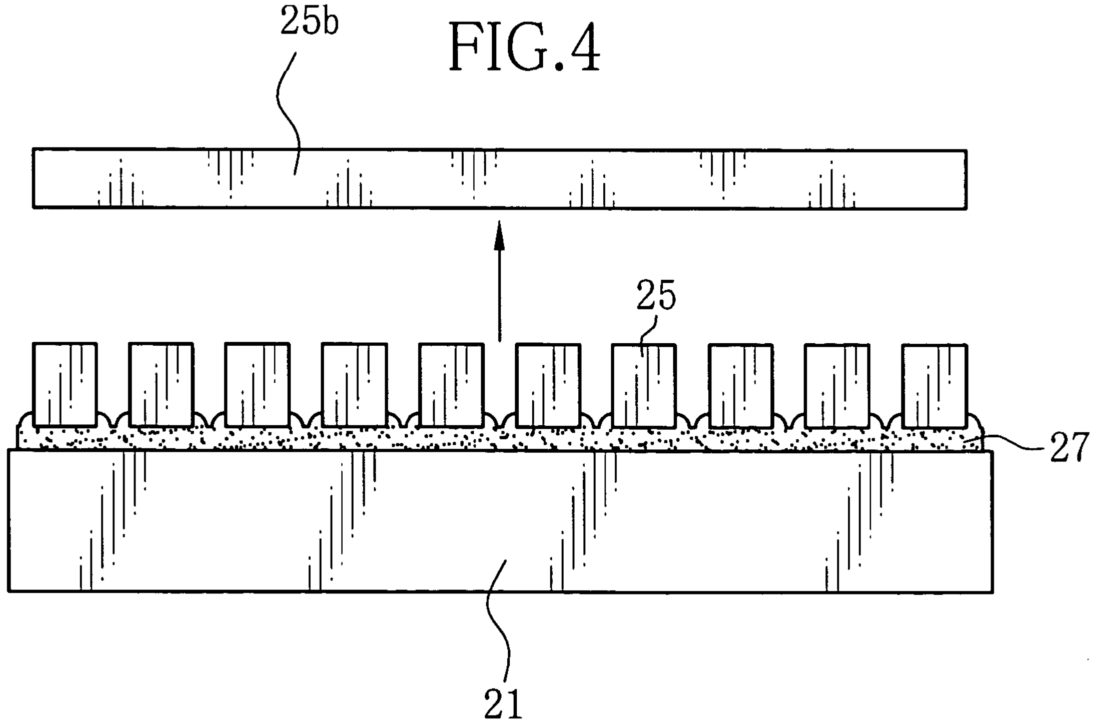
FIG. 4 is an explanatory view showing a process of polishing and removing an upper part of the wafer which was uncuttable in the dicing process.
Figure 5:
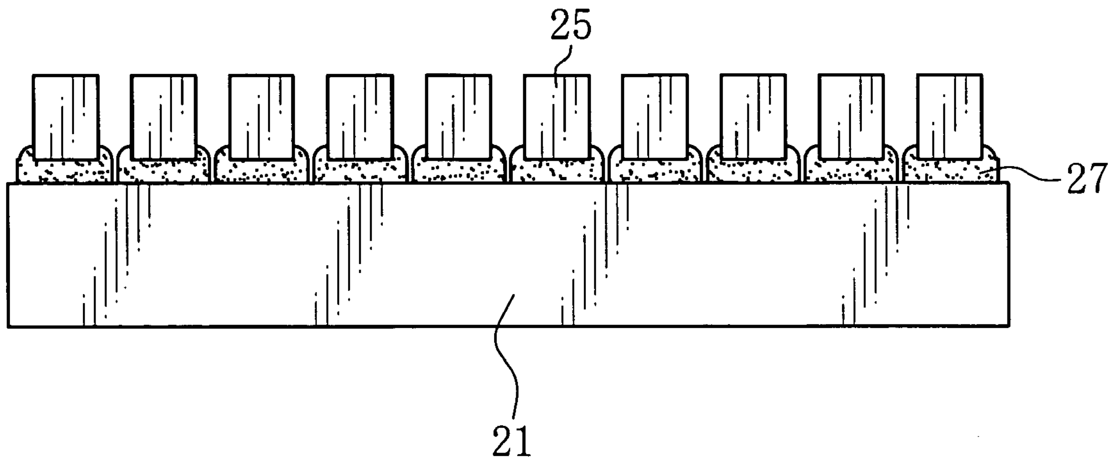
FIG. 5 is an explanatory view showing a process of dividing the silver paste between the piezoelectric elements by a dicing blade to separate the piezoelectric elements from one another.

Next, as shown in FIG. 4, the upper part of the wafer which was left in dicing process is grinded and removed. Subsequently, as shown in FIG. 5, the silver paste 27 between each piezoelectric element 25 is cut by a dicing blade (approximately 20 μm in width) to separate the piezoelectric elements 25 from one another.

Figure 6:
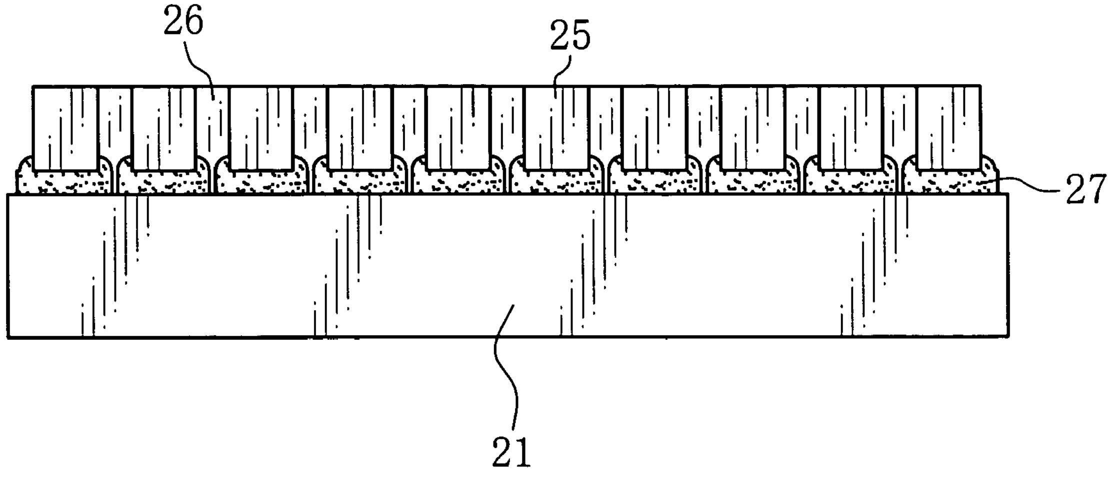
FIG. 6 is an explanatory view showing a process of filling a filling material in gaps between each piezoelectric element.

After cutting the silver paste 27, as shown in FIG. 6, a heat resistant tape is bonded on the piezoelectric elements 25 and the filling materials 26 are filed in the gaps between the piezoelectric elements 25. At last, the common electrode 31 and the acoustic impedance matching layer 23 and the like are overlaid, and the backing material 21 is curved to correspond to the curved surface of the supporting member 20 then bonded to the supporting member 20.

To capture an ultrasonic image inside a body, the ultrasonic probe 2 is inserted into the body, and an aimed internal body part is searched whilst observing the optical image obtained by the imaging device on an endoscope monitor. When the tip 2*a* of the ultrasonic probe 2 reaches the aimed internal part of the living body and a command to capture an ultrasonic image is entered, ultrasounds are generated from the ultrasonic transducer array 10. The ultrasounds scan the living body, and echo from the living body is accordingly received by the ultrasonic transducer array 10. Since the lower part of the side face 25*a* of each piezoelectric element 25 is surrounded by the silver paste 27, the vibration of each piezoelectric element 25 in its width direction is restrained.

The echo from the living body is converted through the ultrasound observing device into an ultrasonic image, which is displayed on the monitor. While observing the optical image or the ultrasonic image, the wearing needle 13 is manipulated to pick up a sample of the aimed internal body part.

As described so far, the lower part of the side face 25*a* of each piezoelectric element 25 is surrounded by the silver paste 27 used for bonding the piezoelectric elements 25 to the backing material 21, therefore the vibrations of the piezoelectric elements 25 in the width direction can be restrained without extra manufacturing cost. Consequently, the vibration action of the piezoelectric elements 25 in the thickness direction is stabilized and it is possible to improve acoustic characteristics of the ultrasonic transducer array.

Moreover the piezoelectric elements 25 are tightly bonded to the backing material 21 since each piezoelectric element 25 is surrounded by the silver paste 27. Therefore, it is possible to improve workability when the backing material 21 is curved and bonded to the curved face of the supporting member 20, and it is also possible to enhance product reliability of the ultrasonic probe 2.

In a convex electronic scanning type as described above or a radial electronic scanning type having a plurality of ultrasonic transducers concentrically arranged, when the ultrasonic transducer array is arranged on the base having curvature, the ultrasonic transducer array is necessary to be bonded with the base plate thereof being curved backward. There is a problem that the ultrasonic transducer is peeled off from the base plate if the ultrasonic transducer is not tightly bonded to the base plate, which causes a negative effect on production yield and manufacturing cost. According to the present invention, the above problem can be easily solved as described herein.

Figure 7:
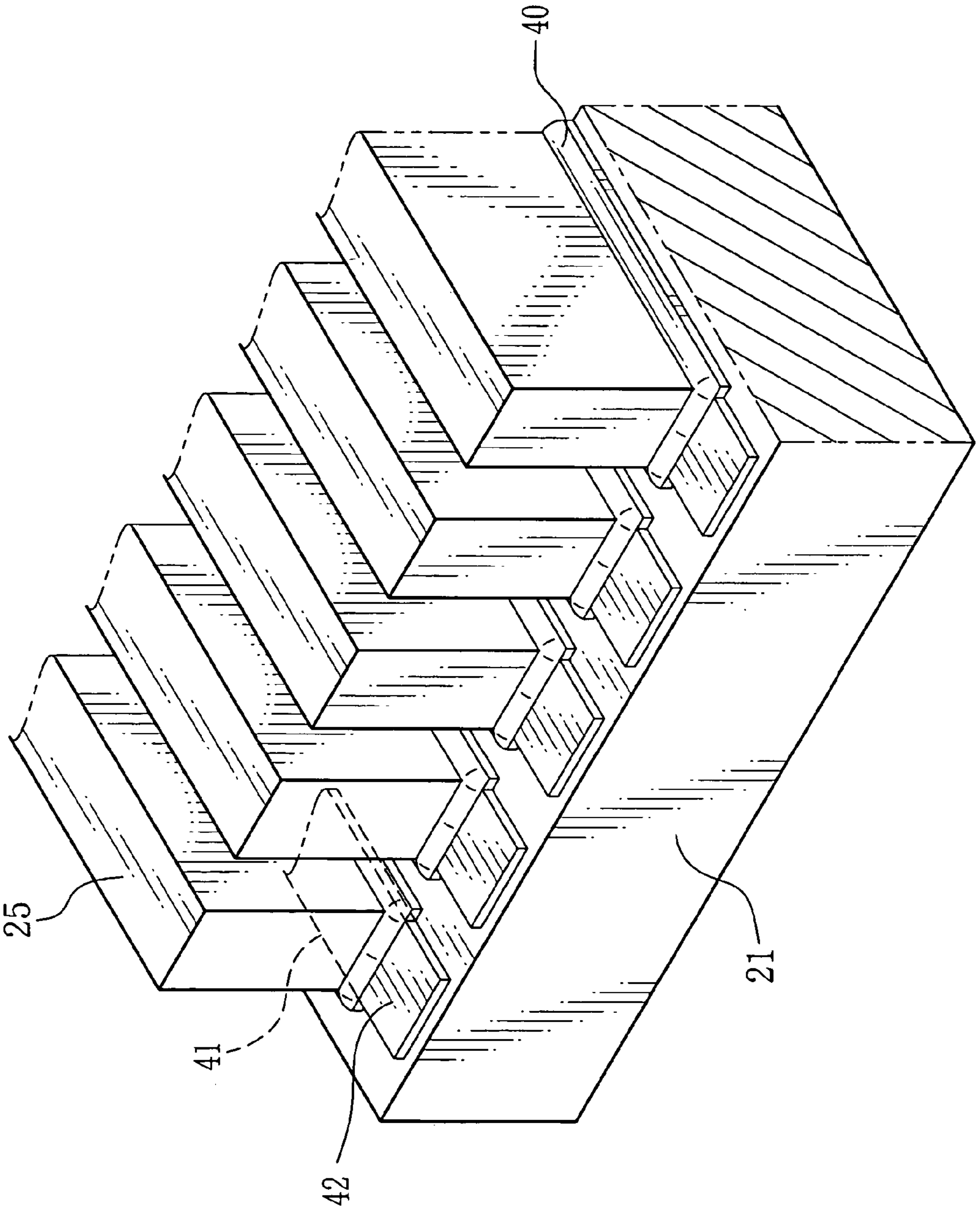
FIG. 7 is a perspective view showing an example that an insulating adhesive is used in place of the silver paste.

If the ultrasonic transducer array 10 is one-dimensional array, an insulating adhesive 40 may be used in place of the silver paste 27 as shown in FIG. 7. In FIG. 7, a backing material 21, piezoelectric elements 25, insulating adhesive 40, conductive plates 41 and terminals 42 are shown. An epoxy resin, a urethane resin, or a silicon resin such as, for example, silicone rubber (product name, produced by Shin-Etsu Chemical Co., Ltd.) may be used for the insulating adhesive 40. In this case, conductive plates 41 made of copper and the like are attached to individual electrodes 30 (exemplary embodiments of which are shown in FIGS. 8-11) of the piezoelectric elements 25, and they are elongated to have terminals 42, exposed from the insulating adhesives 40, for connection to the array wires.

Figure 8:
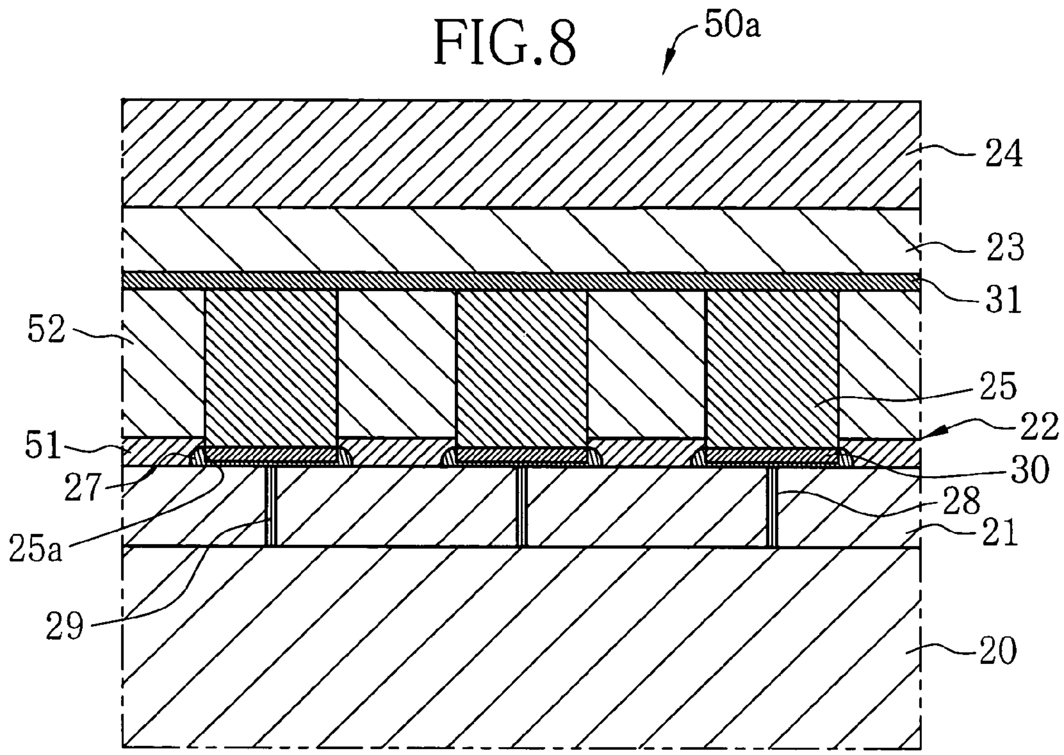
FIG. 8 is an enlarged sectional view showing an example that a lower part of the side face of each piezoelectric element is filled with a rigid filling material.
Figure 9:
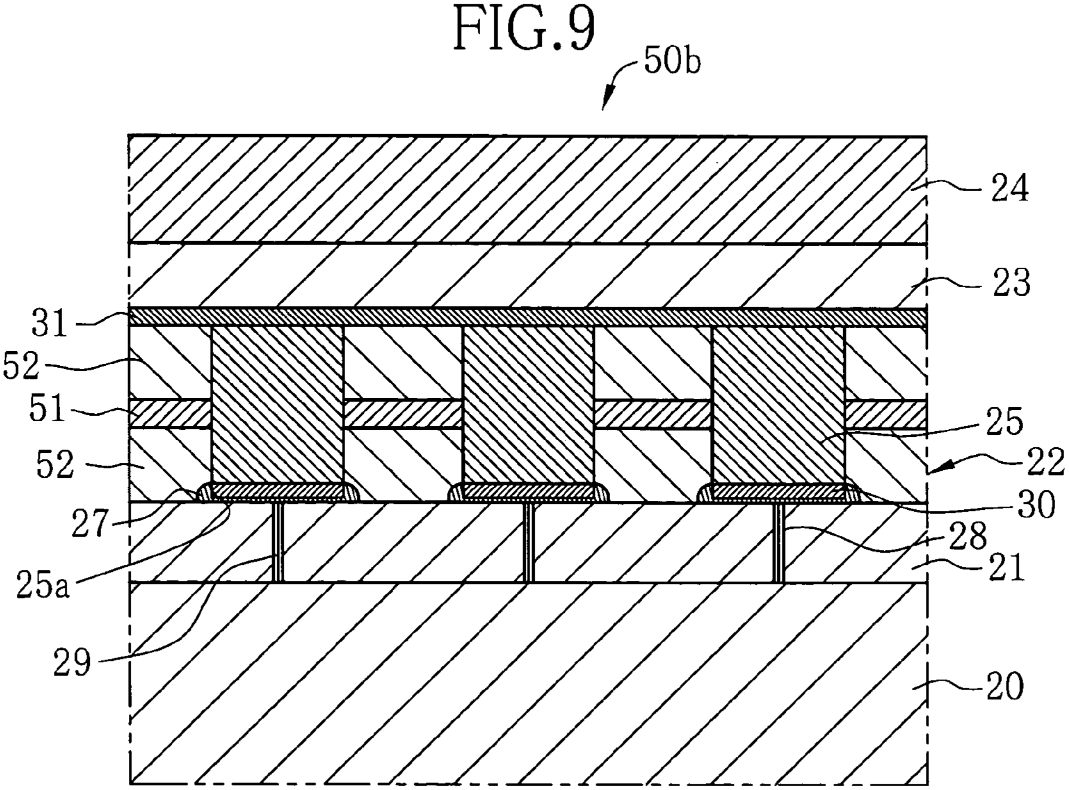
FIG. 9 is an enlarged sectional view showing an example that the rigid filling material is filled around a middle part of the side face of each piezoelectric element.
Figure 10:
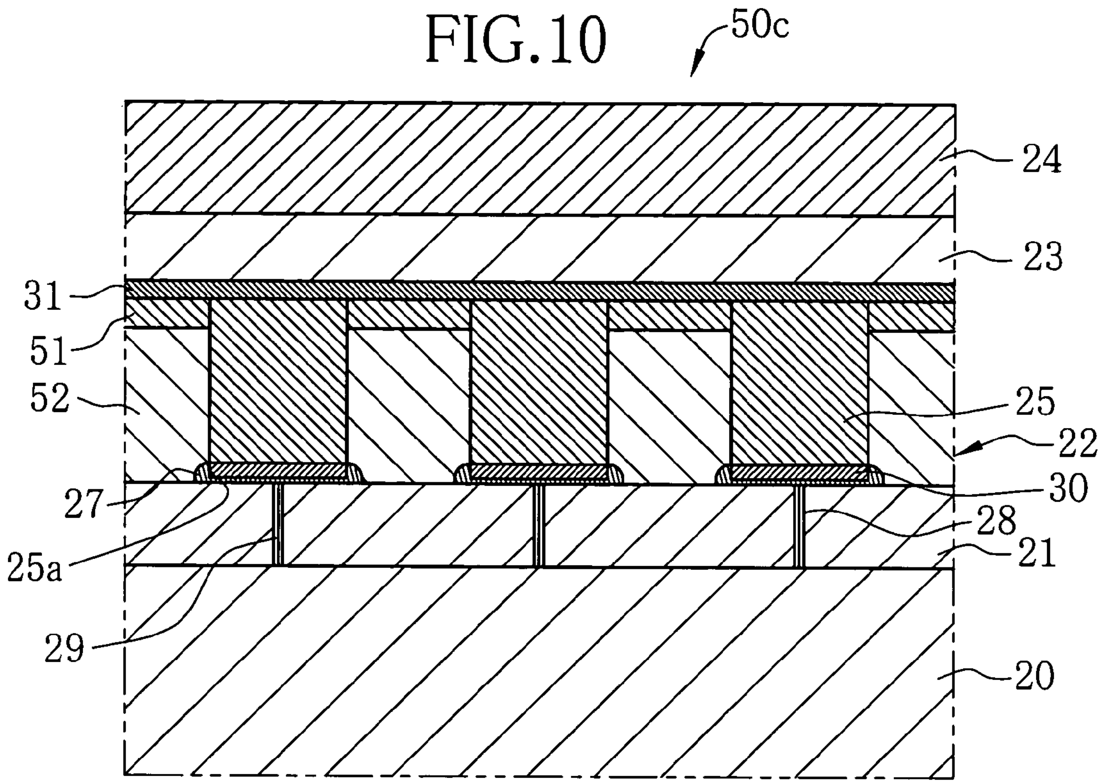
FIG. 10 is an enlarged sectional view showing an example that the rigid filling material is filled around an upper part of each piezoelectric element.

The filling material 26 is useful for restraining vibration in a lateral direction of the piezoelectric elements 25 (in a direction perpendicular to the thickness direction). FIGS. 8 to 10 show embodiments of the filling material.

That is to say that, in the ultrasonic transducer 50*a* in FIG. 8, the area around the lower side of the side face 25*a* of each piezoelectric element 25 surrounded by the silver paste 27 is filled with a rigid filling material 51, and the other area is filled with a soft filling material 52. In the ultrasonic transducer 50*b* in FIG. 9, an area around the middle part of the side face of each piezoelectric element 25 is filled with the rigid filling material 51, and the other areas are filled with the soft filling materials 52. In the ultra sonic transducer 50*c* in FIG. 10, an area around the upper part of the side face of each piezoelectric element 25 is filled with the rigid filling material 51, and the other areas are filled with the soft filling material 52. Thus, the vibrations of the piezoelectric elements 25 in the width direction can be restrained by using different types of filling materials.

Next, a filling method of the materials 51 and 52 will be explained by taking the ultrasonic transducer 50*a* in FIG. 8 for instance. All the gaps between the piezoelectric elements 25 are firstly filled up with the rigid material 51. Then, the rigid filling material 51 is removed by a dicing blade except for the area around the lower sides of the side faces 25*a* of the piezoelectric elements 25, and the soft filling material 52 is filled in the spaced area. It is noted that, for example an epoxy resin is used for the rigid filling material 51, and a urethane resin and a silicon resin are used for the soft filling material 52.

A table 1 shows electro mechanical coupling factors k33 of the piezoelectric elements 25 incorporated in individual ultrasonic transducers 50*a*, as shown in FIG. 8, each of which has different thickness ratio of the filling materials 51 and 52. The epoxy resin and urethane resin are respectively used for the filling materials 51 and 52, and resonance frequency Fr and anti-resonance frequency Fa of the different piezoelectric elements 25 are measured at several times to calculate k33 from the obtained values of the resonance frequency Fr and anti-resonance frequency Fa. According to the table 1, k33 is 0.65 when the thickness ratio of the filling material 51 to the filling material 52 is 1:1 to 1:3, whereas k33 is 0.60 when the thickness ratio of the filling material 51 to the filling material 52 is 1:0 (epoxy resin 100%). It is found out that the vibrations of the piezoelectric elements 25 in the width direction are restrained if the thickness ratio is set within 1:1 to 1:3.

TABLE 1

| RATIO (EPOXY RESIN: URETHANE RESIN) | RESONANCE FREQUENCY Fr [MHz] | ANTI-RESONANCE FREQUENCY Fr [MHz] | ELECTRIC MACHINE COUPLING FACTOR k33 | k33 AVERAGE |
|---|---|---|---|---|
| 1:0 | — | — | 0.60 | — |
| 1:1 | 2.18 | 2.74 | 0.65 | 0.65 |
| | 2.14 | 2.72 | 0.66 | |
| | 2.15 | 2.69 | 0.64 | |
| | 2.11 | 2.73 | 0.68 | |
| | | . | | |
| | | . | | |
| | | . | | |
| 1:3 | 2.11 | 2.66 | 0.65 | 0.65 |
| | 2.13 | 2.61 | 0.62 | |
| | 2.11 | 2.69 | 0.66 | |
| | 2.12 | 2.69 | 0.66 | |
| | | . | | |
| | | . | | |
| | | . | | |

Figure 11:
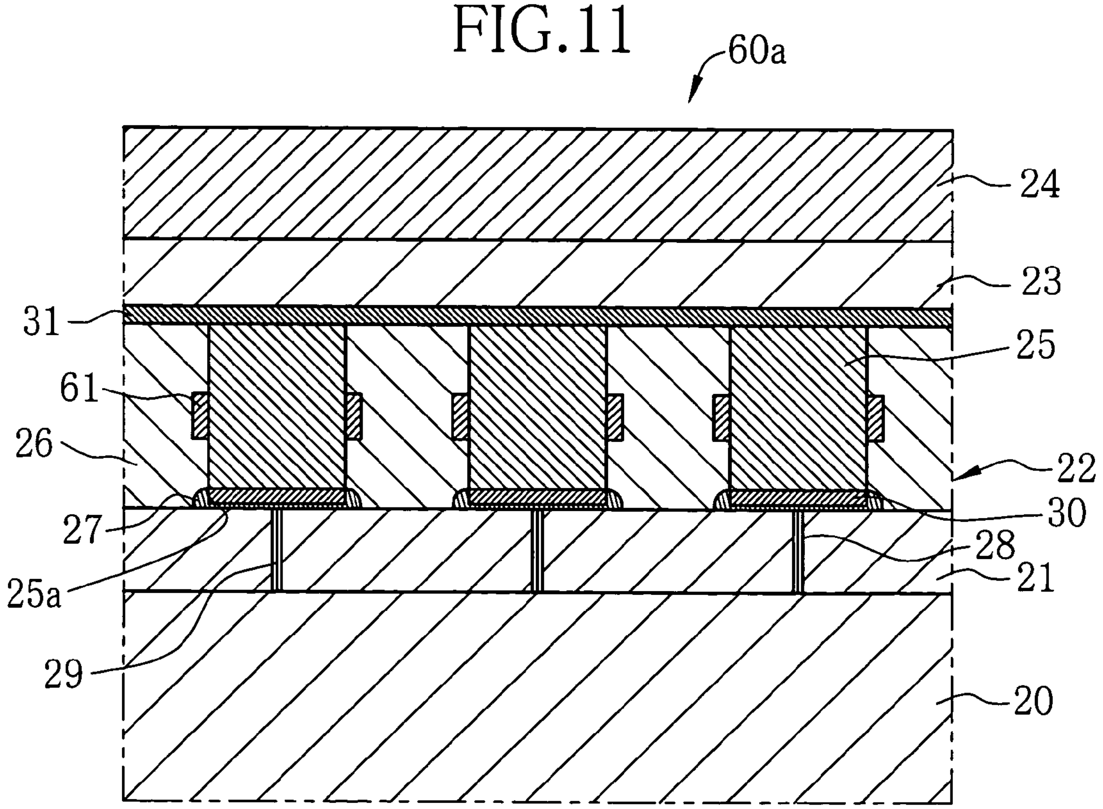
FIG. 11 is an enlarged sectional view showing an example that the side faces of the piezoelectric elements are connected on the central part to one another by beams.
Figure 12:
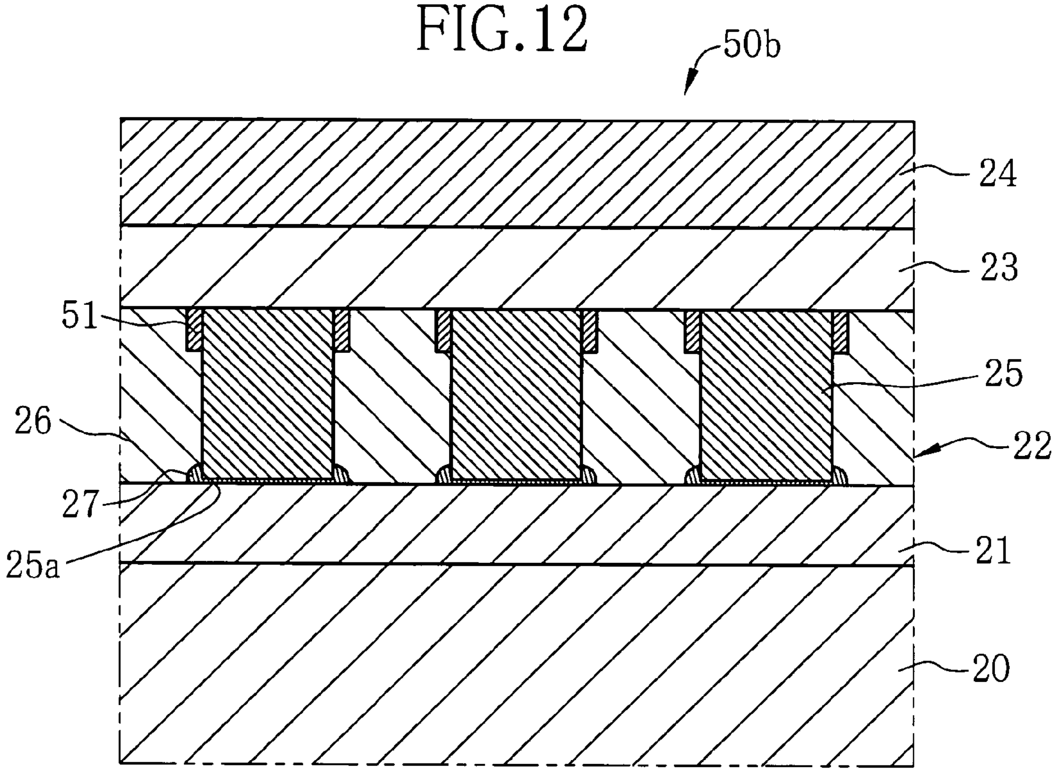
FIG. 12 is an enlarged sectional view showing an example that the side faces of the piezoelectric elements are connected on the upper part to one another by beams.
Figure 13:
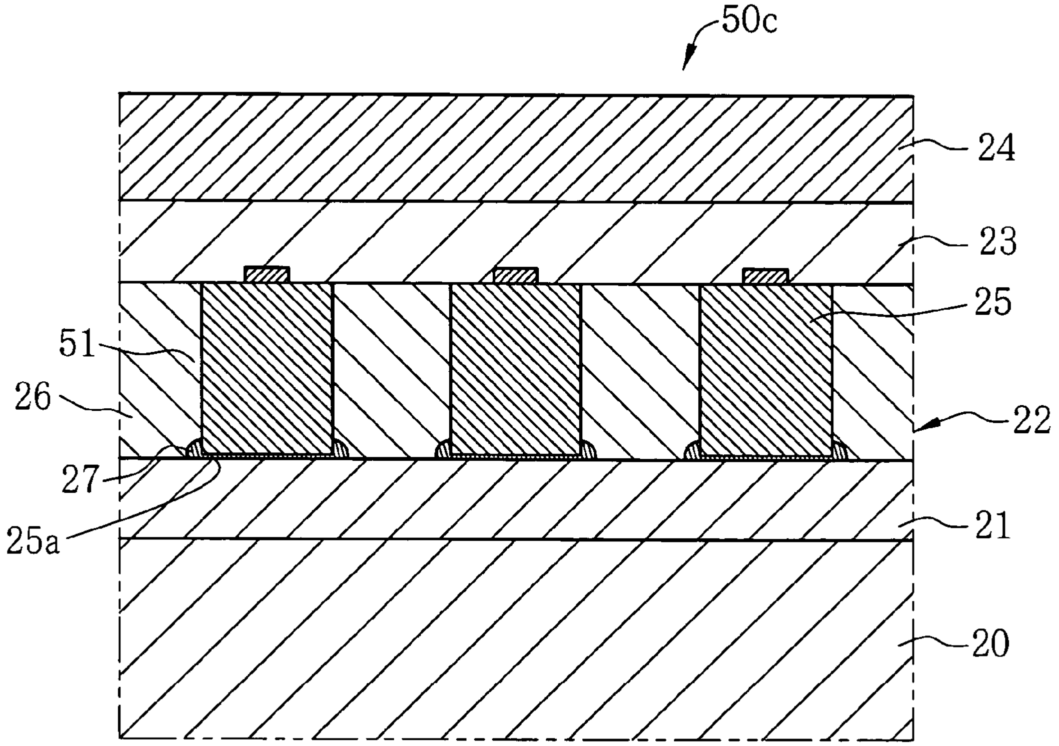
FIG. 13 is an enlarged sectional view showing an example that the upper faces of the piezoelectric elements are connected to one another by beams.

FIGS. 11 to 13 show ultrasonic transducers 60*a* to 60*c* according to other embodiments of the present invention. In the ultrasonic transducers 60*a* in FIG. 11, the side faces of the piezoelectric elements 25 are mutually connected on the central part by beams 61. In the ultrasonic transducers 60*b* in FIG. 12, the upper part of each piezoelectric element 25 is connected by the beam 61. In the ultrasonic transducers 60*c* in FIG. 13, the upper face of each piezoelectric element 25 is connected by the beam 61. If the two-dimensional array is used in the ultrasonic transducers 60*a* to 60*c*, the beams 61 are crossed in the form of parallel cross when seen from the above.

Moreover, the conductive bond material as typified by the silver paste 27 used in the above embodiments has conductivity approximately $3.1\times10^{-4}$ [Ω·cm], preferably $10\times10^{-2}$ to $10\times10^{-4}$ [Ω·cm]. However, the range of the conductivity is not limited to the above, the conductivity may be in the range of approximately $10\times10^{14}$ [Ω·cm] at the normal temperature of 25 degrees, or the conduction-electron concentration may be in the range of $10^{12}$ [$cm^{-3}$ ] to $10^{24}$ [$cm^{-3}$]. That is to say that, a bond material made mostly of silicon, which is a semiconductor, may be used if it is conductive.

In the above embodiments, the convex electronic scanning type ultrasonic transducer arrays 10, 50*a* to 50*c* and 60*a* to 60*c* are described, but the present invention is applicable to, for example, a radial electronic scanning type ultrasonic transducer array including a plurality of ultrasonic transducers concentrically arranged. Furthermore, in addition to the ultrasonic transducer array 10 as mentioned in the above embodiments, the present invention is applicable to an actuator for driving a focusing lens or a zoom lens of a camera, and to other vibrator arrays such as a vibration-type gyroscope used in an angular velocity sensor.

Although the present invention has been fully described by the way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A manufacturing method of a vibrator array having a base plate on which a plurality of vibrators is arranged in an array form, comprising steps of:

subdicing a wafer to form a plurality of said vibrators;

applying bond material to said base plate;

bonding the bottom of each said vibrator to said wafer by said bond material in a manner that a lower part of a side face of each said vibrator is surrounded by said bond material;

disposing a beam member along at least one of a central part and an upper part of the side face of each said vibrator, said beam member connecting each said vibrator; and removing an upper portion of said wafer, which connects the upper parts of said vibrators, to separate said vibrators.

2. A manufacturing method of a vibrator array as claimed in claim 1, wherein said bond material has conductivity.

3. A manufacturing method of a vibrator array as claimed in claim 1, wherein said bond material is applied to said base plate in which coating thickness of said bond material is 10 to 20 % of thickness of said vibrator.

4. A manufacturing method of a vibrator array as claimed in claim 1, wherein said bond material is silver paste or an insulating adhesive.

5. A manufacturing method of a vibrator array as claimed in claim 1, wherein a filling material is further filled in between each said vibrator.

6. A manufacturing method of a vibrator array as claimed in claim 5, wherein said filling material has a multilayer structure of different rigidity.

7. A manufacturing method of a vibrator array as claimed in claim 6, wherein rigidity of a layer of said filling material at the base plate side is greater than that of the other layers of said filling material.

8. A manufacturing method of a vibrator array as claimed in claim 6, wherein said filling material has double layer, wherein thickness ratio of a layer of said filling material at the base plate side to the other layer of said filling material is 1:1 to 1:3.

* * * * *